(12) United States Patent
Ahn

(10) Patent No.: US 11,547,576 B2
(45) Date of Patent: Jan. 10, 2023

(54) STRUCTURE OF POROUS SPINAL IMPLANT

(71) Applicants: Kyoung Gee Ahn, Seoul (KR); GBS Commonwealth Co., Ltd., Seoul (KR); PMT Republic, Inc., Walnut, CA (US)

(72) Inventor: Kyoung Gee Ahn, Seoul (KR)

(73) Assignees: Kyoung Gee Ahn, Seoul (KR); GBS Commonwealth Co., Ltd., Seoul (KR); PMT Republic. Inc., Walnut, CA (US)

(*) Notice: Subject to any disclaimer, the term of this patent is extended or adjusted under 35 U.S.C. 154(b) by 0 days.

(21) Appl. No.: 17/169,278

(22) Filed: Feb. 5, 2021

(65) Prior Publication Data

US 2021/0244548 A1 Aug. 12, 2021

(30) Foreign Application Priority Data

Feb. 6, 2020 (KR) .................. 10-2020-0014235

(51) Int. Cl.
*A61F 2/44* (2006.01)
*A61F 2/30* (2006.01)

(52) U.S. Cl.
CPC ...... *A61F 2/447* (2013.01); *A61F 2002/3093* (2013.01); *A61F 2002/30784* (2013.01); *A61F 2002/30841* (2013.01); *A61F 2002/30985* (2013.01)

(58) Field of Classification Search
CPC .. A61F 2/44; A61F 2/442; A61F 2/447; A61F 2002/30784; A61F 2002/30841; A61F 2002/3093; A61F 2002/30985

USPC .......................................... 623/17.11–17.16
See application file for complete search history.

(56) References Cited

U.S. PATENT DOCUMENTS

| | | | | |
|---|---|---|---|---|
| 6,830,570 B1* | 12/2004 | Frey | ................... | A61B 17/1642 623/17.16 |
| 10,517,739 B2* | 12/2019 | Ryan | ...................... | A61F 2/442 |
| 2008/0154377 A1* | 6/2008 | Voellmicke | ........... | A61F 2/4611 623/17.16 |
| 2010/0228296 A1* | 9/2010 | Vraney | ................... | A61F 2/447 606/279 |
| 2010/0268349 A1* | 10/2010 | Bianchi | ................... | A61F 2/446 623/23.51 |
| 2011/0082551 A1* | 4/2011 | Kraus | ................... | A61F 2/3662 623/17.11 |
| 2011/0224796 A1* | 9/2011 | Weiland | ................... | B22F 10/38 427/2.27 |
| 2012/0185047 A1* | 7/2012 | Wooley | ................... | A61F 2/4455 427/2.26 |

(Continued)

*Primary Examiner* — Jessica Weiss
(74) *Attorney, Agent, or Firm* — McCoy Russell LLP

(57) ABSTRACT

Provided is a structure of a porous spinal implant including a cage body inserted between adjacent vertebral bodies and divided by an upper surface, a lower surface, a left surface, a right surface, a front surface, and a rear surface, a plurality of vertical pores formed on the upper surface and the lower surface of the cage body, and a plurality of horizontal structures stacked on the left surface and the right surface of the cage body, wherein the plurality of vertical pores and the plurality of horizontal structures are each formed in a pattern that repeats in up-down, left-right, and front-rear directions. The structure of a porous spinal implant is capable of reducing strength of a cage body close to that of a vertebral body.

13 Claims, 7 Drawing Sheets

(56) References Cited

U.S. PATENT DOCUMENTS

| | | | |
|---|---|---|---|
| 2013/0116793 A1* | 5/2013 | Kloss | A61F 2/442 623/17.16 |
| 2013/0131812 A1* | 5/2013 | Ganey | A61B 17/80 623/17.16 |
| 2017/0216036 A1* | 8/2017 | Cordaro | A61F 2/44 |
| 2018/0243097 A1* | 8/2018 | Jones | B33Y 10/00 |
| 2018/0256336 A1* | 9/2018 | Mueller | A61F 2/2846 |
| 2019/0000636 A1* | 1/2019 | Kim | A61F 2/447 |
| 2019/0254840 A1* | 8/2019 | Gray | A61F 2/447 |

* cited by examiner

STRUCTURE OF POROUS SPINAL IMPLANT

CROSS-REFERENCE TO RELATED APPLICATION

The present application claims priority to Korean Patent Application No. 10-2020-0014235 filed on Feb. 6, 2020. The entire contents of the above-listed application is hereby incorporated by reference for all purposes.

TECHNICAL FIELD

The following disclosure relates to a structure of a spinal implant, and in particular, to a structure of a porous spinal implant which is output to a three-dimensional (3D) printer so that a certain pattern may be repeated to thereby realize an elastic force similar to an existing vertebral body.

BACKGROUND

Structural problems may occur in the spine, such as congenital, degenerative, or for other reasons such as accidents, problems in stable arrangement, or narrowing of the spacing between vertebral bodies. Typical spinal diseases include spinal deformities, vertebral fractures, herniation of an intervertebral disc, spinal stenosis, facet hypertrophy, and the like and such spinal diseases require a surgical treatment when symptoms worsen and conservative care is difficult.

Spinal fusion of a surgical treatment method is a surgical procedure of removing an intervertebral disc in which a spinal disorder has occurred, inserting a spinal cage (or a spinal implant) between the vertebral bodies to secure a space to grow and enter the bone for agglutination, increasing a gap between the vertebral bodies to reduce pain, and restoring lordosis of the spine to maintain stability of the spine.

In general, the spinal cage used in the spinal fusion has a hollow formed therein, so that a bone chip is inserted therein, and as the bone chip is regenerated, bone fusion is made between upper and lower vertebral bodies.

Various types of spinal cages have been developed according to treatment approaches, and development of shapes for restoring biomechanical stability of the spine while being implantable in the human body has also been made in various ways.

The spinal cage has a structure of a solid body formed of a metal material such as titanium or a titanium alloy having mechanical properties suitable for supporting a human load because a certain interval should be maintained between the vertebral bodies.

However, the conventional spinal cage has a problem in that facing surfaces of a vertebral body and a neighboring vertebral body subside by upper and lower surfaces of the spinal cage, after the spinal fusion procedure is completed.

In addition, the conventional spinal cage cannot prevent the subsidence phenomenon occurring in the process of bone fusion and may not implement a buffering effect at all against the pressure and shock according to a user's weight or posture change.

The contents described as the related art have been provided only to assist in understanding the background of the present disclosure and should not be considered as corresponding to the related art known to those having ordinary skill in the art.

SUMMARY

An exemplary embodiment of the present invention is directed to providing a structure of a porous spinal implant capable of reducing strength of a cage body to be close to that of a vertebral body.

Another exemplary embodiment of the present invention is directed to providing a structure of a porous spinal implant in which a plurality of vertical pores are formed on upper and lower surfaces of a cage body and a plurality of horizontal structures are formed on left and right surfaces of the cage body to improve a fusion rate.

Technical objects to be achieved by the present invention are not limited to the aforementioned technical objects, and other technical objects not mentioned above may be evidently understood by a person having ordinary skill in the art to which the present invention pertains from the following description.

In one general aspect, a structure of a porous spinal implant may include: a cage body inserted between adjacent vertebral bodies and divided by an upper surface, a lower surface, a left surface, a right surface, a front surface, and a rear surface; a plurality of vertical pores formed on the upper surface and the lower surface of the cage body; and a plurality of horizontal structures stacked on the left surface and the right surface of the cage body, wherein the plurality of vertical pores and the plurality of horizontal structures are each formed in a pattern that repeats in up-down, left-right, and front-rear directions.

The vertical pores may be formed by perforating the upper and lower surfaces of the cage body in a circular or elliptical shape in an up-down direction.

The horizontal structures may have a columnar shape having a predetermined width, having a hexagonal cross-section, and having a hollow inner side, and may be arranged in a left-right direction.

A ratio of lengths of a shorter axis to a longer axis of the vertical pores may be 1:1 to 1:3.

Lengths of a shorter axis or a longer axis of the vertical pores may be 300 to 700 μm.

A plurality of teeth may protrude from the upper and lower surfaces of the cage body, and the plurality of vertical pores may be formed on the plurality of teeth vertically in a penetrating manner.

The plurality of vertical pores may be formed in a remaining region of the upper surface and the lower surface of the cage body in which the plurality of teeth are not formed in a penetrating manner.

An angle of a pair of vertices of the plurality of horizontal structures disposed at the front and rear may be 120° or less.

The plurality of the horizontal structures may have an edge thickness of 0.3 to 1.5 mm.

A length of the horizontal structures in a front-rear direction may be 3 to 9 mm and a length of the horizontal structures in an up-down direction may be 2 to 6 mm.

An arc-shaped first dispersion portion having a predetermined curvature may be formed at each vertex inside an edge of the horizontal structures.

A second dispersion portion may be formed in a straight flat shape at each vertex inside the edge of the horizontal structures.

A front inclined surface having a predetermined angle with respect to a central portion may be formed on the front surface of the cage body.

A guide hole penetrating a central portion of the cage body may be formed on the front surface of the cage body in the front-rear direction.

A step portion having a width relatively narrower than a width between the left and right surfaces of the cage body may be formed to be depressed at a central portion of the rear surface of the cage body.

Both sides of the step portion may be formed as stepped inclined surfaces having a predetermined angle with respect to the central portion.

The rear surface of the cage body may have a fastening hole penetrating through a central portion thereof in the front-rear direction and having a thread formed therein.

The fastening hole may be disposed coaxially with a guide hole in the front-rear direction.

The structure of a porous spinal implant may further include: a pair of hollows penetrating a central portion of the cage body; and a partition disposed between the pair of hollows in the front-rear direction to partition the pair of hollows, wherein the plurality of horizontal structures are arranged on a side portion of the partition in the left-right direction to penetrate the side portion of the partition, and the plurality of horizontal structures are stacked even on the front surface and the rear surface of the cage body.

Other features and aspects will be apparent from the following detailed description, the drawings, and the claims.

DETAILED DESCRIPTION

Figure 1:
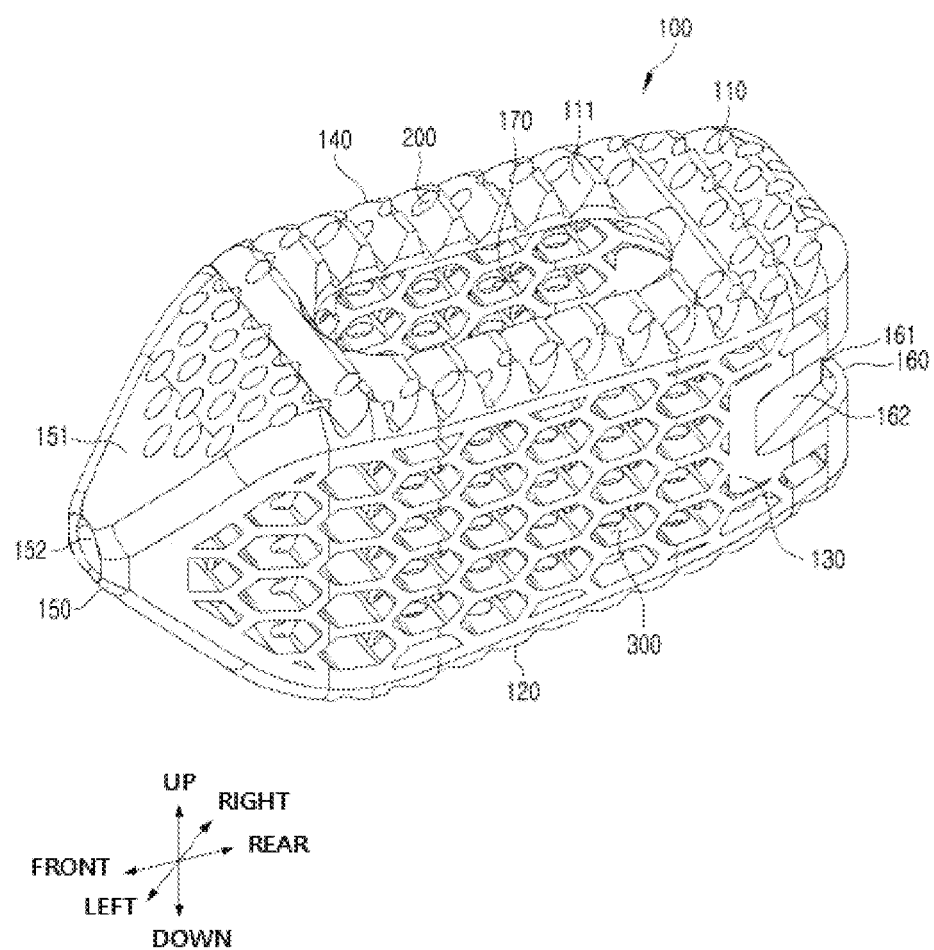
FIG. 1 is a view showing the overall appearance of a structure of a porous spinal implant according to an exemplary embodiment.

Hereinafter, exemplary embodiments of the present disclosure will be described in detail with reference to the accompanying drawings so that a person skilled in the art to which the present invention pertains to easily implement the invention. The present disclosure may be modified in various different ways and may not be limited to the exemplary embodiments described herein.

In order to clearly describe the present invention, a portion irrelevant to a description of the present invention will be omitted, and like reference numerals refer to like elements throughout.

Terms or words used in the disclosure and claims should not be limited and construed as common or dictionary meanings, and should be construed as meanings and concepts according to the technical spirit of the present invention based on the principle that the inventor can appropriately define the concept of each term for describing the invention in the best way.

FIG. 1 is a view showing an overall appearance of a structure of a porous spinal implant according to an exemplary embodiment of the present invention.

As shown, the structure of a porous spinal implant according to the present invention includes a cage body 100 inserted between adjacent vertebral bodies. The cage body 100 is divided into an upper surface 110, a lower surface 120, a left surface 130, a right surface 140, a front surface 150, and a rear surface 160.

The cage body 100 is a medical device used in spinal fusion, and is inserted between vertebral bodies to maintain a gap between the vertebral bodies, and serves to secure a space for bone to grow and enter for fusion.

A hollow 170 is formed at a central portion of the cage body 100, and the hollow 170 is filled with an autograft, allograft, or synthetic bone to promote a bone growth.

The cage body 100 is formed of a material such as metal powder or ceramic powder excellent in biocompatibility and is preferably manufactured using selective laser melting (SLM) type 3D printer equipment.

In the illustrated exemplary embodiment, the cage body 100 is formed in a long bullet shape in the front-rear direction, but without being limited thereto, the cage body 100 may be formed in various shapes such as a flat shape, a curved shape, and a disk shape.

A plurality of vertical pores 200 are formed in the upper surface 110 and the lower surface 120 of the cage body 100. The vertical pores 200 are formed by perforating the cage body 100 in an up-down direction and in a circular or elliptical shape. In the present invention, the vertical pores 200 are formed in a pattern that repeats in the front-rear and left-right directions.

The upper surface 110 and the lower surface 120 of the cage body 100 may have a plurality of teeth 111 to dig into upper and lower vertebral bodies so that the cage body 100 may have a constant fixing force between the vertebral bodies. The plurality of teeth 111 stably maintains a position of the cage body 100 at an initial stage of a spinal fusion procedure.

The plurality of vertical pores 200 may be formed to vertically penetrate a region in which the teeth 111 are formed in the upper surface 110 and the lower surface 120 of the cage body 100. That is, in the present invention, the plurality of vertical pores 200 may also be formed on the teeth 111.

Of course, the plurality of vertical pores 200 may be formed to penetrate the other regions of the upper surface 110 and the lower surface 120 in which the plurality of teeth 111 are not formed.

In addition, the plurality of vertical pores 200 may also be formed on a portion or the entirety of an upper portion and a lower portion of the front surface 150 and the rear surface 160 of the cage body 100, as well as on the upper surface 110 and the lower surface 120 of the cage body, according to shapes of the cage body 100.

A plurality of horizontal structures 300 is stacked on the left surface 130 and the right surface 140 of the cage body 100. The horizontal structures 300 have a hexagonal cross-section and are formed in the shape of an empty column having a predetermined width. The horizontal structures 300 are arranged in the left-right direction on the cage body 100 and are formed in a pattern that repeats in the up-down direction.

Like the plurality of vertical pores 200, the plurality of horizontal structures 300 may also be formed on a portion or the entirety of a left side or a right side of the front surface 150 and the rear surface 160 of the cage body 100, as well as on the left surface 130 and the right surface 140 of the cage body 100, according to shapes of the cage body 100.

In addition, the plurality of horizontal structures 300 may not completely form a hexagonal cross-section according to sizes or outer shapes of the cage body 100 and may have a partially unstable form.

The vertical pores 200 may be formed on a portion having a predetermined width of the horizontal structures 300, as well as on the upper surface 110 and the lower surface 120 of the cage body 100, so that the left structure 300 may be open in both the up-down direction and left-right direction.

In other words, in the present invention, holes of the horizontal structures 300 formed in the up-down direction and holes of the horizontal structures 300 formed in the left-right direction are advantageous for a bone growth through pores, thereby significantly improving a fusion rate.

Figure 2:
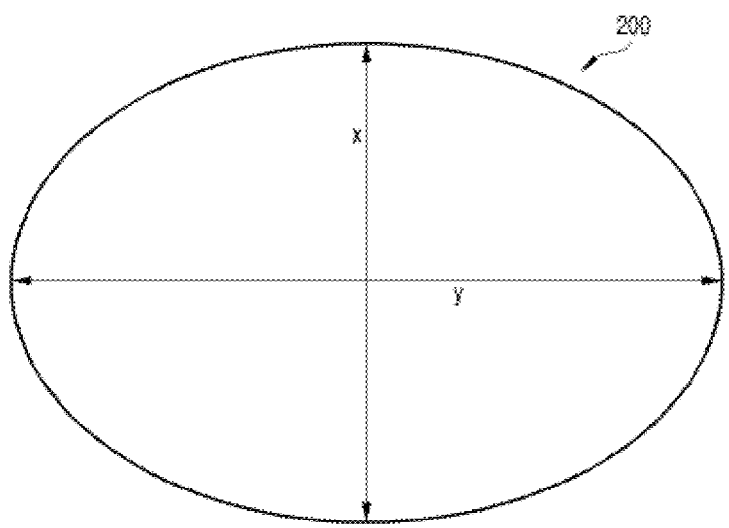
FIG. 2 is a view showing a shape of vertical pores according to an exemplary embodiment.

FIG. 2 is a view showing an exemplary shape of a vertical pore according to an exemplary embodiment of the present invention.

The vertical pore 200 perforated on the upper surface 110 and the lower surface 120 of the cage body 100 may be formed to have a circular or elliptical cross-section. In the illustrated exemplary embodiment, an ellipse is used as an example.

As described above, the vertical pore 200 may be formed anywhere on the front surface 150, the rear surface 160, the teeth 111, a width-directional portion of the horizontal structures 300, and the like, as well as on the upper surface 110 and the lower surface 120 of the cage body 100, as long as the vertical pores penetrate the cage body 100 vertically.

The vertical pore 200 may increase a contact area with an end plate of the vertebral body to improve subsidence stability, reduce stiffness of the cage body 100 to be close to stiffness of a patient's bone or polyetheretherketone (PEEK) product, and enable a smooth bone fusion.

The ratio of a length of a shorter axis (x) to a longer axis (y) of the vertical pores 200 is preferably 1:1 to 1:3, and a length of the shorter axis (x) or the longer axis (y) may be 300 to 700 μm.

This is because the ratio and length as above correspond to the ratio and length of the vertical pore 200 at which a bone fusion most actively takes place in a human body in a spinal fusion procedure.

FIG. 3 is a view showing an exemplary form of horizontal structures according to an exemplary embodiment of the present invention.

Figure 3A:
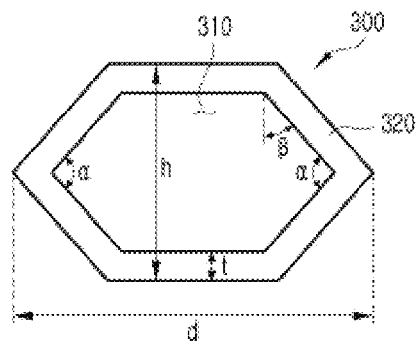
FIGS. 3A-3C are views showing forms of horizontal structures according to an exemplary embodiment.
Figure 3B:
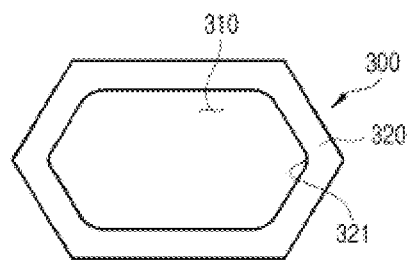
Figure 3C:
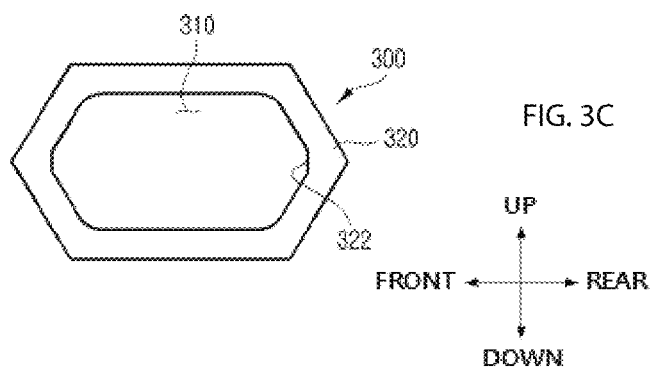

Specifically, FIG. 3(a) is a view illustrating a vertex angle of a horizontal structure according to an exemplary embodiment of the present invention, FIG. 3(b) is a view illustrating a first dispersion portion of a horizontal structure according to an exemplary embodiment of the present invention, and FIG. 3(c) is a view illustrating a second dispersion portion of a horizontal structure according to an exemplary embodiment of the present invention.

As illustrated, the horizontal structure 300 according to the present invention is formed by perforating the left surface 130 and the right surface 140 of the cage body 100 in the left-right direction and includes a horizontal pore 310 having a hexagonal cross-section and a horizontal edge 320 disposed to surround the horizontal pore along a circumference of the horizontal pore and having a predetermined thickness t.

The horizontal edge 320 includes six corners surrounding the horizontal pore 310, and each corner is disposed between one horizontal pore 310 and adjacent horizontal pore 310 so as to be shared by the both horizontal pores 310 (see FIG. 1).

The horizontal pore 310 having a hexagonal cross-section has a pair of facing vertices disposed at the front and rear and two pairs of facing vertices respectively disposed at the top and bottom, totaling six vertices.

Here, an angle α of the pair of facing vertices disposed at the front and rear of the horizontal pore 310 is preferably 120° or less. Accordingly, an angle β obtained by subtracting 90° from the angle of the two pairs of facing vertices disposed at the top and bottom of the horizontal pore 310 may be 30° or greater.

Here, in the present invention, the cage body 100 may be self-standing without sagging by the horizontal structure 300 without a separate frame, and in order for the horizontal structure 300 to be self-standing and stacked, the angle β obtained by subtracting 90° from the angle of two pairs of the facing vertices arranged at the top and bottom, respectively, should be 30° or greater.

In other words, if the angle α of the pair of facing vertices disposed at the front and rear of the horizontal pore 310, respectively, is 120° or greater, the angle β obtained by subtracting 90° from the angle of the two pairs of facing vertices each arranged at the top and bottom of the horizontal pore 310 may be less than 30°, so that the horizontal structure 300 may not be stacked on its own.

As described above, the horizontal edge 320 is disposed along a circumference of the horizontal pore 310 and has the predetermined thickness t. Here, the thickness t of the horizontal edge 320 is preferably 0.3 to 1.5 mm.

This is because, when the horizontal structure 300 having a hexagonal cross-section is formed in a pattern that repeats in the up-down direction and the front-rear direction as in the present invention, the cage body 100 may have structural stiffness similar to that of a product formed of a PEEK material when the thickness t of the horizontal edge 320 is 0.3 to 1.5 mm.

If the thickness t of the horizontal edge 320 is less than 0.3 mm, the cage body 100 may not support a load of a human body by maintaining a certain distance between the two vertebral bodies, and if the thickness t exceeds 1.5 mm, elastic force of the cage body 100 is so small that the vertebral body may subside or a buffering effect against pressure and impact cannot be implemented at all.

Meanwhile, a length d of the horizontal structure 300 including the horizontal edge 320 in a front-rear direction is preferably 3 to 9 mm, and a vertical length h is preferably 2 to 6 mm.

As shown in FIG. 3(b), a first dispersion portion 321 having an arc shape having a predetermined curvature is formed at each vertex inside the horizontal edge 320 of the horizontal structure 300, and as shown in FIG. 3(c), a second dispersion portion 322 having a straight flat shape is formed at each vertex inside the horizontal edge 320 of the horizontal structure 300.

As described above, the cage body 100 may be self-standing without sagging by the horizontal structure 300 even without a separate frame, and the first dispersion portion 321 or the second dispersion portion 322 serves to disperse stress applied to each vertex of the horizontal structure 300.

Figure 4:
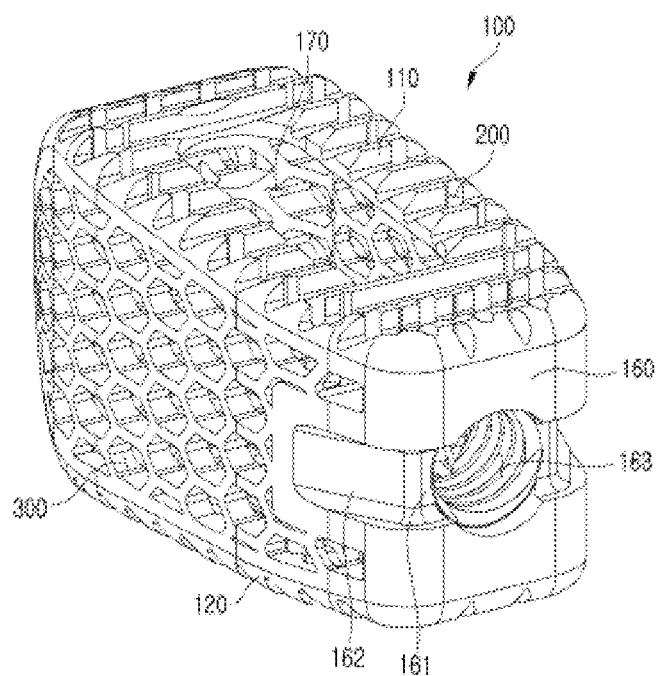
FIG. 4 is a rear view showing a structure of a porous spinal implant according to an exemplary embodiment.
Figure 5:
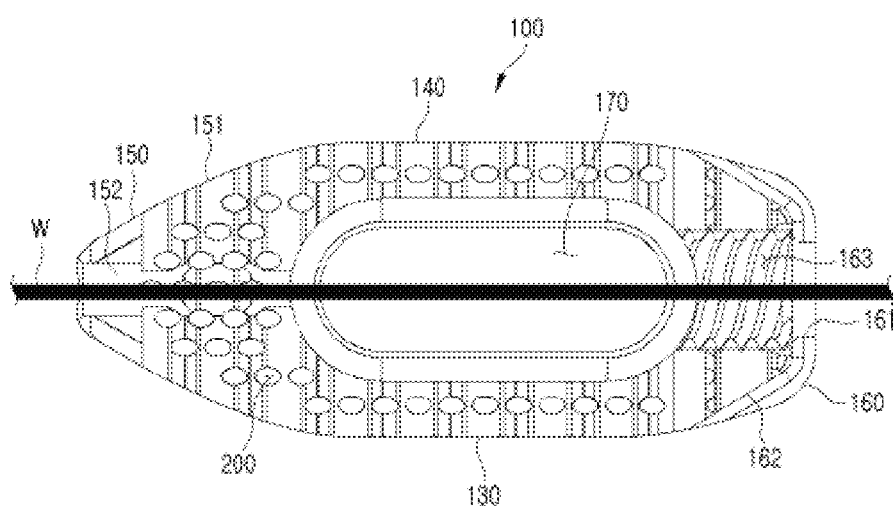
FIG. 5 is a cross-sectional view of a structure of a porous spinal implant according to an exemplary embodiment, taken with respect to an axis in a front-rear direction.
Figure 6:
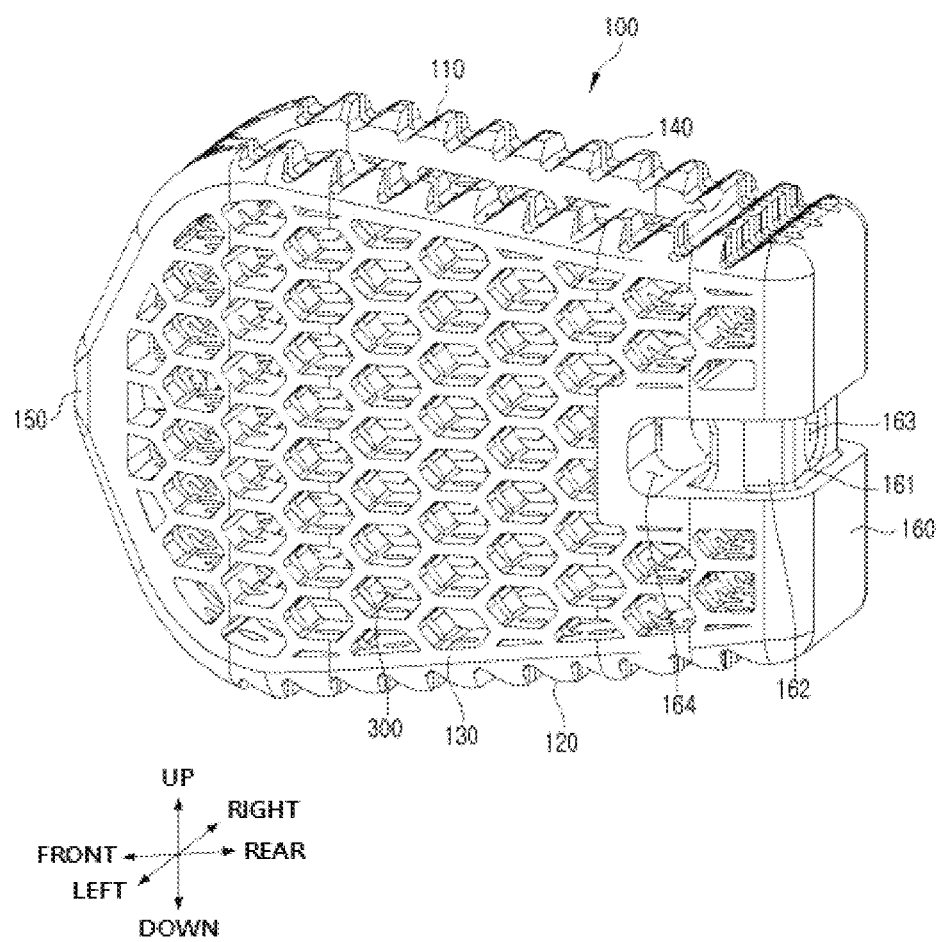
FIG. 6 is a side view of a structure of a porous spinal implant according to another exemplary embodiment.

FIG. 4 is a rear view showing a structure of a porous spinal implant according to an exemplary embodiment, FIG. 5 is a cross-sectional view of a structure of a porous spinal implant according to an exemplary embodiment, taken with respect to an axis in a front-rear direction, and FIG. 6 is a side view of a structure of a porous spinal implant according to another exemplary embodiment.

First, as shown in FIG. 1, a front inclined surface 151 having a predetermined angle with respect to a central portion may be formed on the front surface 150 of the cage body 100. In addition, a guide hole 152 is formed in a penetrating manner at a central portion of the front surface 150 of the cage body 100 in the front-rear direction.

That is, in the front surface 150 of the cage body 100, the upper, lower, left, and right sides configure the front inclined surface 151 with respect to the guide hole 152 at the central portion to form a converging square pyramid.

Here, the vertical pore 200 may be formed on the front inclined surfaces 151 disposed on the upper and lower portions of the front surface 150 of the cage body 100 in a penetrating manner, and the front surface of the cage body 100, and the horizontal structure 300 may be formed on the front inclined surfaces 151 disposed on the left and right sides of the front surface 150.

As shown in FIG. 4, a step portion 161 having a width narrower than a width between the left surface 130 and the right surface 140 of the cage body 100 is formed to be recessed at a central portion of the rear surface 160 of the cage body 100.

The step portion 161 is disposed on a front side relative to the rear surface 160 of the cage body 100, and as shown in FIG. 5, a rear end of the step portion 161 has a width relatively narrower than the width between the left surface 130 and the right surface 140 of the cage body 100, and a front end of the step portion 161 has the same width as the width between the left surface 130 and the right surface 140 of the cage body 100.

In other words, since there is a difference in width between the rear end and the front end of the step portion 161, both side portions of the step portion 161 are formed as a stepped inclined surface 162 having a predetermined angle with respect to the central portion.

The rear surface 160 of the cage body 100 is formed with a fastening hole 163 penetrating the central portion in the front-rear direction and having a thread formed therein. That is, the fastening hole 163 is formed at the rear surface 160 of the cage body 100, the step portion 161 is formed based on the fastening hole 163, and the stepped inclined surface 162 is formed at both side portions of the step portion 161.

Meanwhile, as shown in FIG. 6, the rear surface 160 of the cage body 100 may additionally have a through portion 164 penetrating the left surface 130 and the right surface 140 of the cage body in the left-right direction.

The through portion 164 is disposed in a direction perpendicular to the fastening hole 163, and the through portion 164, the fastening hole 163, the step portion 161, and the stepped inclined surface 162 are organically formed to perform a function of allowing an insertion mechanism to be easily fastened to the cage body 100 when the cage body 100 is inserted between the vertebral bodies.

In addition, as shown in FIG. 5, the fastening hole 163 is disposed coaxially with the guide hole 152 in the front-rear direction, and a wire mechanism W may be inserted through the fastening hole 163 and the guide hole 152. The wire mechanism W serves as a guide when inserting the cage body 100 between the vertebral bodies.

As described above, in the present invention, the plurality of vertical pores 200 formed on the upper surface 110 and the lower surface 120 of the cage body 100 and the plurality of horizontal structures 300 formed on the left surface 130 and the right surface 140 may have an effect of reducing strength of the cage body 100 to be close to stiffness of a patient's vertebral body or a PEEK product.

In addition, in the present invention, the plurality of vertical pores 200 and the plurality of horizontal structures 300 formed on the cage body 100 overall are advantageous for a bone growth through the pores, thus significantly improving a fusion rate.

Figure 7:
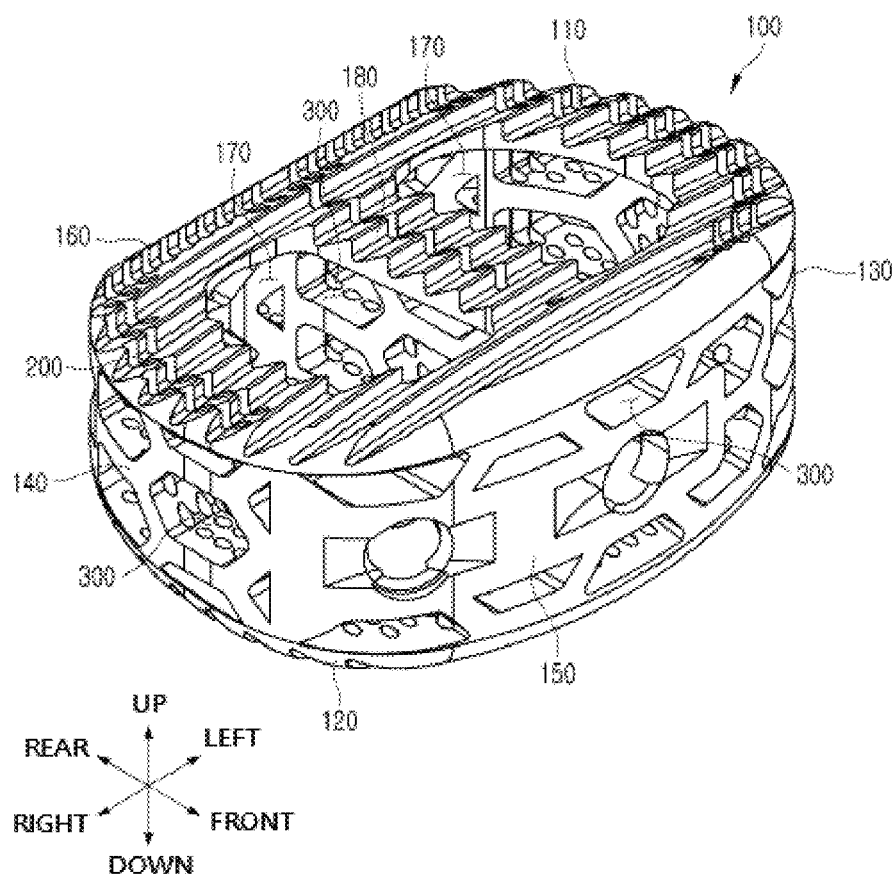
FIG. 7 is an overall view of structure of a porous spinal implant according to another exemplary embodiment.

FIG. 7 is an overall view of structure of a porous spinal implant according to another exemplary embodiment.

As shown, in another exemplary embodiment of the present invention, the cage body 100 is divided into an upper surface 110, a lower surface 120, a left surface 130, a right surface 140, a front surface 150, and a rear surface 160, and a hollow 170 is formed at a central portion of the cage body 100.

As described above, a plurality of vertical pores 200 are formed on the upper surface 110 and the lower surface 120 of the cage body 100. The vertical pores 200 are formed by perforating the cage body 100 in a circular or elliptical shape in the up-down direction. In the present invention, the vertical pores 200 are formed in a pattern that repeats in the front-rear direction and the left-right direction.

In another exemplary embodiment of the present invention, a plurality of horizontal structures 300 are stacked on the left surface 130, the right surface 140, the front surface 150, and the rear surface 160 of the cage body 100. The horizontal structures 300 are formed in a pattern that repeats in the up-down and front-rear directions or in the up-down and left-right directions.

The horizontal structures 300 disposed on the left surface 130 and the right surface 140 of the cage body 100 have a hexagonal cross-section and are formed in a hollow columnar shape having a predetermined width, and the horizontal structures 300 disposed on the front surface 150 and the rear surface 160 of the cage body 100 has a partially cut-away form or in a partially incomplete form.

As described above, the vertical pores 200 are formed not only on the upper surface 110 and the lower surface 120 of the cage body 100 but also on a portion having a predetermined width of the horizontal structures 300, so that the horizontal structures 300 may be open in the left-right direction or in the front-rear direction and may also be open in the up-down direction.

In another exemplary embodiment of the present invention, the hollow 170 is provided as a pair, and a partition 180 is disposed between the hollows to partition the pair of hollows 170. The partition 180 is disposed in the front-rear direction to partition the pair of hollows 170 in the left-right direction.

A plurality of vertical pores 200 are formed on the upper and lower portions of the partition 180 in a penetrating manner, and a plurality of horizontal structures 300 are disposed in the left-right direction on the side of the partition 180 to penetrate the side of the partition.

That is, the partition 180 is also open in both up and down and left and right to help facilitate a bone fusion and reduces stiffness of the cage body 100 to be close to stiffness of a PEEK product.

As described above, in the present invention having the configuration described above, by forming the plurality of vertical pores on the upper and lower surfaces of the cage body and forming the plurality of horizontal structures on the left and right surfaces of the cage body, strength of the cage body may be reduced to be close to stiffness of the patient's vertebral body or a PEEK product.

In addition, in the present invention, since the plurality of vertical pores and the plurality of horizontal structures are formed entirely in the cage body, it is advantageous for a bone growth through the pores to significantly improve a fusion rate.

Further, in the present invention, the guide hole is formed on the front surface of the cage body and the fastening hole is formed on the rear surface so as to be fastened to a wire-shaped instrument, which enables a minimally invasive surgery.

The present invention described above is not limited to the exemplary embodiments described above and the accompanying drawings, and it will be obvious to those skilled in the art to which the present invention pertains that various substitutions, modifications, and changes may be made within the scope of the technical spirit of the present invention.

The invention claimed is:

1. A porous spinal implant, comprising:
a cage body configured to be inserted between adjacent vertebral bodies and comprising an upper surface, a lower surface, a left surface, a right surface, a front surface, and a rear surface;
a plurality of vertical pores formed through the upper surface and the lower surface of the cage body; and
a plurality of stacked horizontal structures formed along the left surface and the right surface of the cage body,
wherein the plurality of vertical pores are formed in a pattern that repeats in a left-right direction and a front-rear direction, and wherein the plurality of horizontal structures are formed in a pattern that repeats in an up-down direction and in the front-rear direction,
wherein a guide hole penetrating a central portion of the cage body is formed in the front surface of the cage body in the front-rear direction and a fastening hole penetrating through a central portion of the cage body with a thread formed therein is formed in the rear surface thereof disposed coaxially with the guide hole, and
wherein a depressed step portion having a width relatively narrower than a width between the left and right surfaces of the cage body is formed in a central portion of the rear surface of the cage body, and both sides of the step portion are formed as stepped inclined surfaces having a predetermined angle with respect to the central portion, each of the stepped inclined surfaces being depressed toward the front surface relative to the rear surface and extending away from the fastening hole and toward the left or right sides at the predetermined angle;
wherein the plurality of vertical pores are formed as perforations in the upper and lower surfaces of the cage body having a circular shape or an elliptical shape in the up-down direction, and
wherein the plurality of horizontal structures are hollow and have a columnar shape with a hexagonal cross-section, a predetermined width, and are arranged in the left-right direction.

2. The porous spinal implant of claim 1, wherein a ratio of a length to a height of each of the plurality of vertical pores is 1.1 to 1.3.

3. The porous spinal implant of claim 1, wherein a length or a height of each of the plurality of vertical pores is 300 to 700 μm.

4. The porous spinal implant of claim 1, wherein the upper and lower surfaces of the cage body each comprise a plurality of teeth, and wherein some of the plurality of vertical pores penetrate the plurality of teeth vertically.

5. The porous spinal implant of claim 4, wherein at least some of the plurality of vertical pores are formed in a region free of any of the plurality of teeth.

6. The porous spinal implant of claim 1, wherein the hexagonal cross-section comprises a pair of vertices having an angle of 120 degrees or less.

7. The porous spinal implant of claim 1, wherein the plurality of horizontal structures have an edge thickness of 0.3 to 1.5 mm.

8. The porous spinal implant of claim 1, wherein a length of each of the plurality of horizontal structures in the front-rear direction is 3 to 9 mm and a length of each of the plurality of horizontal structures in the up-down direction is 2 to 6 mm.

9. The porous spinal implant of claim 1, wherein an arc-shaped portion having a predetermined curvature is formed at a vertex inside an edge of the plurality of horizontal structures.

10. The porous spinal implant of claim 1, wherein a linear portion is formed in a straight flat shape at a vertex inside the edge of the plurality of horizontal structures.

11. The porous spinal implant of claim 1, wherein
a front inclined surface having a predetermined angle with respect to a central portion is formed on the front surface of the cage body.

12. The porous spinal implant of claim 1, wherein a through portion penetrating the left surface and the right surface of the cage body in the left-right direction is further provided adjacent the depressed step portion at the central portion of the rear surface of the cage body.

13. The porous spinal implant of claim 1, further comprising:
a pair of hollows penetrating a central portion of the cage body in the up-down direction; and
a partition disposed between the pair of hollows in the front-rear direction partitioning the pair of hollows, wherein some of the plurality of horizontal structures are arranged on a side portion of the partition in the left-right direction to penetrate the side portion of the partition, and some of the plurality of horizontal structures are stacked on the front surface and the rear surface of the cage body.

* * * * *